(12) United States Patent
Mandell

(10) Patent No.: US 8,696,755 B2
(45) Date of Patent: Apr. 15, 2014

(54) TIBIAL COMPONENT OF AN ARTIFICIAL KNEE JOINT

(76) Inventor: Steven L. Mandell, Loomis, CA (US)

(*) Notice: Subject to any disclaimer, the term of this patent is extended or adjusted under 35 U.S.C. 154(b) by 548 days.

(21) Appl. No.: 12/148,366

(22) Filed: Apr. 17, 2008

(65) Prior Publication Data

US 2009/0265013 A1    Oct. 22, 2009

(51) Int. Cl.
*A61F 2/64*    (2006.01)

(52) U.S. Cl.
USPC .......................................... 623/20.32

(58) Field of Classification Search
USPC ............................................ 623/20.14–20.31
See application file for complete search history.

(56) References Cited

U.S. PATENT DOCUMENTS

| | | | |
|---|---|---|---|
| 4,019,298 A * | 4/1977 | Johnson, IV | 52/590.1 |
| 4,568,348 A | 2/1986 | Johnson | |
| 4,743,261 A * | 5/1988 | Epinette | 623/20.32 |
| 4,963,152 A | 10/1990 | Hofmann | |
| 5,080,674 A * | 1/1992 | Jacobs et al. | 623/20.17 |
| 5,201,881 A * | 4/1993 | Evans | 623/20.28 |
| 5,219,362 A | 6/1993 | Tuke | |
| 5,326,358 A * | 7/1994 | Aubriot et al. | 623/20.28 |
| 5,358,527 A * | 10/1994 | Forte | 623/20.27 |
| 5,413,604 A | 5/1995 | Hodge | |
| 5,486,178 A | 1/1996 | Hodge | |
| 5,549,686 A | 8/1996 | Johnson | |
| 5,702,463 A * | 12/1997 | Pothier et al. | 623/20.32 |
| 5,702,464 A * | 12/1997 | Lackey et al. | 623/20.32 |
| 5,702,466 A * | 12/1997 | Pappas et al. | 623/20.29 |
| 5,749,876 A | 5/1998 | Duvillier | |
| 5,824,103 A * | 10/1998 | Williams | 623/20.32 |
| 5,871,545 A * | 2/1999 | Goodfellow et al. | 623/20.28 |
| 5,925,049 A | 7/1999 | Gustilo | |
| 6,013,103 A * | 1/2000 | Kaufman et al. | 623/20.15 |
| 6,126,692 A * | 10/2000 | Robie et al. | 623/20.32 |
| 6,436,135 B1 * | 8/2002 | Goldfarb | 623/1.39 |
| 6,652,588 B2 * | 11/2003 | Hayes et al. | 623/20.32 |
| 6,797,005 B2 * | 9/2004 | Pappas | 623/20.27 |
| 7,160,330 B2 * | 1/2007 | Axelson et al. | 623/20.14 |
| 7,625,407 B2 * | 12/2009 | Akizuki et al. | 623/20.32 |
| 2002/0055784 A1 * | 5/2002 | Burstein et al. | 623/20.28 |
| 2002/0072802 A1 * | 6/2002 | O'Neil et al. | 623/20.33 |
| 2004/0102786 A1 | 5/2004 | Grundei | |
| 2004/0204765 A1 * | 10/2004 | Fenning et al. | 623/20.29 |
| 2005/0107886 A1 * | 5/2005 | Crabtree et al. | 623/20.24 |
| 2006/0142869 A1 * | 6/2006 | Gross | 623/20.34 |
| 2006/0195196 A1 * | 8/2006 | Pendleton et al. | 623/20.34 |
| 2008/0058945 A1 * | 3/2008 | Hajaj et al. | 623/20.14 |
| 2008/0114464 A1 * | 5/2008 | Barnett et al. | 623/20.33 |
| 2008/0119939 A1 * | 5/2008 | Termanini | 623/20.27 |
| 2009/0222014 A1 * | 9/2009 | Bojarski et al. | 606/88 |
| 2009/0265011 A1 * | 10/2009 | Mandell | 623/20.15 |

* cited by examiner

*Primary Examiner* — David Isabella
*Assistant Examiner* — Randy Shay
(74) *Attorney, Agent, or Firm* — Heisler & Associates

(57) ABSTRACT

A tibial component of an artificial knee joint is provided which cooperates with a femoral component to allow pivoting rotation of the artificial knee joint in either a clockwise or counterclockwise direction. The tibial component includes a plate with a tapered dovetail rib thereon which allows an insert to be removably secured thereto to act as a meniscal structure for the tibial component. The insert has a proximal surface with left and right wells therein that include valleys to guide rotation of one condylar leg of a femoral component while holding a second condylar leg of the femoral component within the other one of the wells, allowing pivoting rotation in either direction. A nesting of the insert into a portion of the plate minimizes an overall height of the tibial component and minimizing tibial bone resection, while providing a greater resistance to shear forces upon the knee joint.

18 Claims, 10 Drawing Sheets

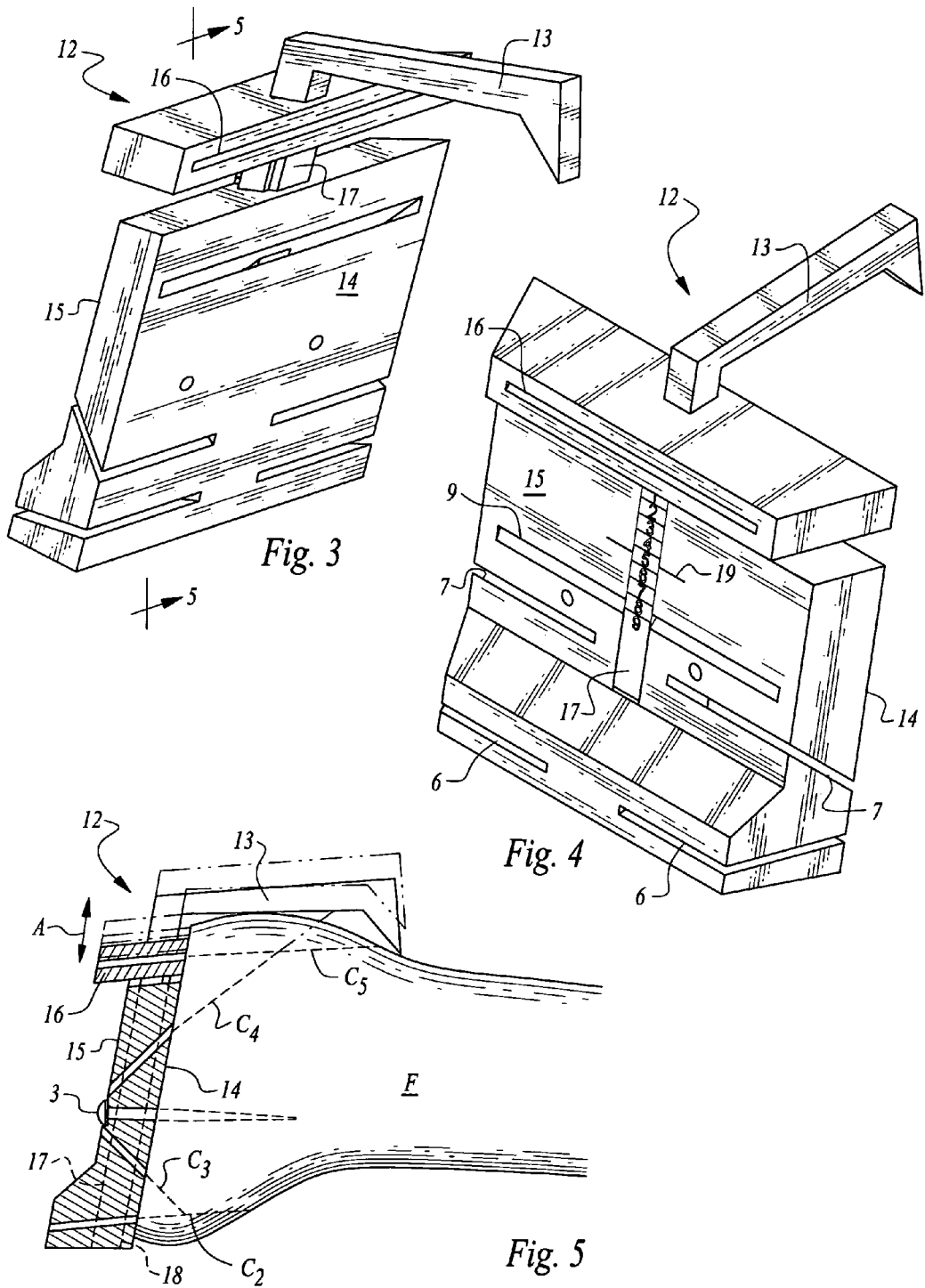

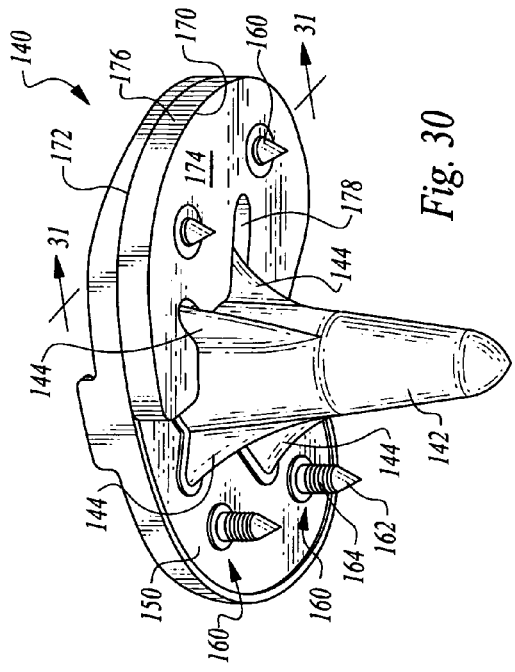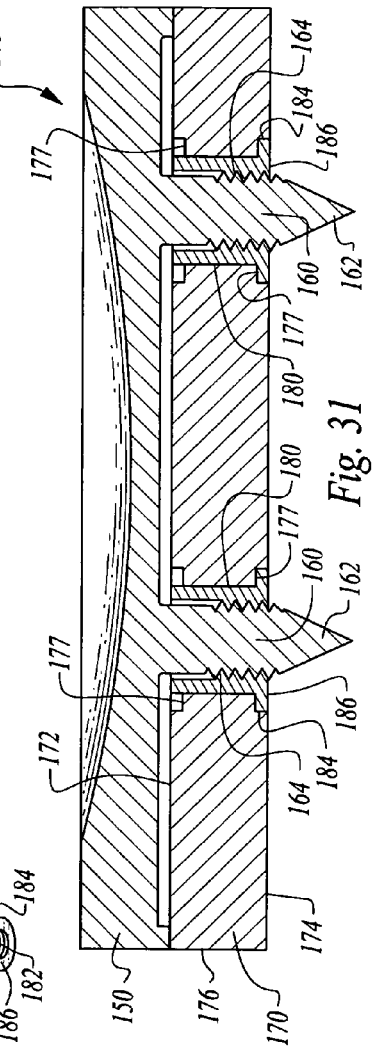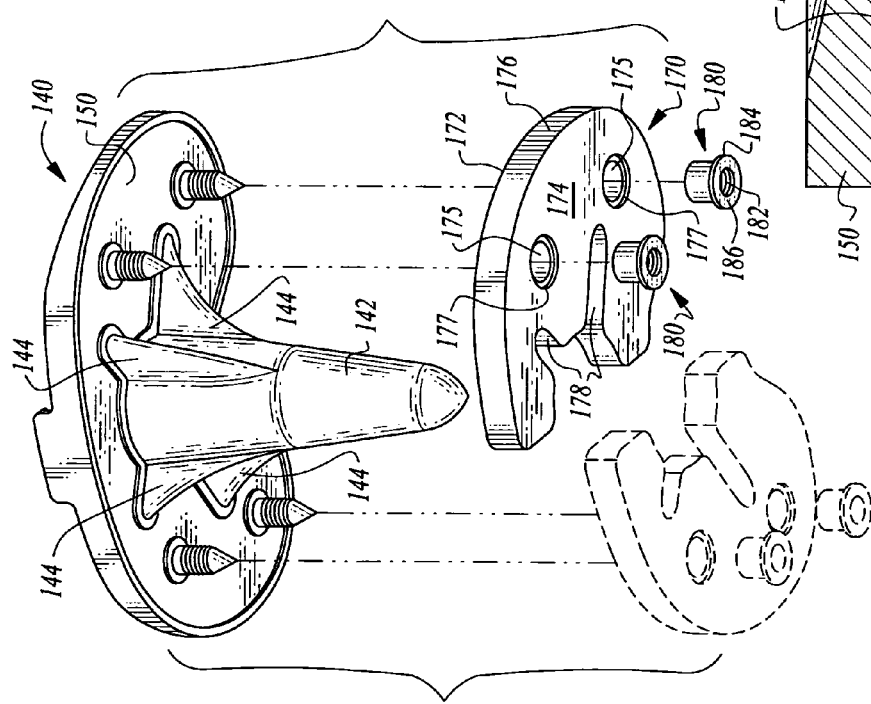

TIBIAL COMPONENT OF AN ARTIFICIAL KNEE JOINT

CROSS-REFERENCE TO RELATED APPLICATIONS

The following patent application is being filed in coordination with another patent application having a very similar disclosure and related to other portions of a common artificial knee joint. This other corresponding application is entitled "FEMORAL COMPONENT OF AN ARTIFICIAL KNEE JOINT," has the same inventor, was filed on the same day and has Ser. No. 12/148,363.

FIELD OF THE INVENTION

The following invention relates to surgical implants placed within a knee of a patient to function as an artificial knee joint. More particularly, this invention relates to artificial knee joints which include a femoral component, a tibial component and a patellar component which exhibit a simplified femoral component, femoral component sizing, bone preparation procedures, tibial component meniscal insert low wear characteristics and dual direction knee pivoting rotation function therein.

BACKGROUND OF THE INVENTION

Human knee joints endure exceptional loads and a wide variety of loading scenarios throughout the life of an individual. While the human knee joint is capable of supporting most of these typical loads under normal conditions for the life of the individual, in certain circumstances the human knee joint suffers degraded performance. For instance, injury can occur to the knee causing the knee to not fully repair itself, or not being fully repairable through medical intervention, such that it becomes beneficial to replace the knee joint with an artificial knee joint. In other circumstances, degenerative disease can act on the natural knee joint to degrade its performance in an irreversible fashion, such that replacement of the natural knee joint with an artificial knee joint is indicated.

Artificial knee joints are well known in the literature and have come into widespread use. In general, such artificial knee joints include a femoral component, a tibial component and a patellar component. The distal end of the femur is surgically prepared to have the distal end thereof have a contour matching an internal box surface of the femoral component. The femoral component is then attached to the distal end of the femur. Similarly, the proximal end of the tibia is prepared, typically by cutting a flat proximal surface on the proximal end of the tibia, and the tibial component is attached to this proximal end of the tibia. Muscles and ligaments surrounding the knee are disturbed as little as possible so that they can continue to function in the same manner that they do with a natural knee joint. Proximal surfaces of the tibial component and distal surfaces of the femoral component abut each other and are designed to facilitate articulation relative to each other in the same way that the distal end of a natural femur articulates relative to the proximal end of a natural tibia. Typically, an insert of materials somewhat more flexible and resilient than metal is attached to a proximal end of the tibial component, with other portions of the tibial component formed of a more rigid material, such as titanium or cobalt chrome. This insert in some ways duplicates the function of a natural meniscus within a natural knee joint, and helps to minimize friction in the articulation of the femoral component relative to the tibial component.

Numerous drawbacks have been noted with prior art artificial knee joints and for which this invention strives to provide a significant and beneficial improvement. For instance, artificial knee joints are known for being somewhat complex to implant, and most particularly the femoral component. In particular, the distal end of the femur must be extensively shaped to properly mate with facets on the internal box face of the femoral component.

In the prior art, the surgeon must make numerous very precise cuts on the distal end of the femur and these cuts vary based on the particular geometry of the facets on the internal box face of the femoral component. Because different human bodies have different sizes, various different femoral components having different sizes must be considered before selecting the particular femoral component. Typically, a cutting jig or other specialized tool must be selected that matches with the femoral component selected so that the cuts are properly made.

As a result, the surgeon, manufacturer or an associated health care facility must maintain an extensive inventory of femoral cutting jigs for potential use in an artificial knee joint surgical procedure. Such extensive inventory of cutting jigs is expensive to maintain, requires additional space within the surgery room or nearby, and presents the greater possibility of problems during or after surgery. Furthermore, an increase of such cutting jigs is more difficult to clean and sterilize which increases the potential for infection, in turn resulting in a less than fully desirable outcome. U.S. Pat. Nos. 5,925,049 and 5,749,876 both describe a femoral cutting instrument sizer that allows a single tool to be used for a set of femoral components of different sizes however both devices are cumbersome and complicated to use. Accordingly, a need exists for an artificial knee joint which has a femoral component which is one of a set of femoral components of different sizes which share as many shape and size characteristics as possible, as well as a single tool which can easily make the necessary cuts for all different femoral component sizes.

Another problem with known prior art artificial knee joints is that they cannot duplicate the large amount of flexion produced by a natural human knee joint and still provide sufficient contact between the artificial femur and the tibial component. Conventional artificial knee joints are limited in further flexion because they typically cause the femur or structure coupled to the femur to abut the tibia or structures coupled to the tibia to prevent further flexion. Accordingly, a need exists for an artificial knee joint which can provide as much flexion as possible to more fully mimic a natural knee joint in performance.

Another problem with known prior art artificial knee joints is their inability or difficulty in facilitating knee pivoting rotation in both clockwise and counterclockwise directions. A natural knee joint is capable of a small amount of pivoting rotation. Such pivoting rotation is particularly desirable when a person is walking along a curving path.

Some artificial knee joints, such as those taught by Hodge (U.S. Pat. No. 5,413,604) allow for pivoting rotation of the medial condyle about the lateral condyle, but not rotation of the lateral condyle. Furthermore, other artificial knee joints, such as those taught by Kaufman (U.S. Pat. No. 6,013,103) and Tuke (U.S. Pat. No. 5,219,362) describe pivoting rotation of the lateral condyle about the medial condyle. Accordingly, a need exists for complete replication of function of a natural knee joint, including pivoting rotation in both directions.

Another problem with known prior art artificial knee joints is the need for the insert or other meniscal structure to exhibit a minimum thickness for suitable wear characteristics and duration, while minimizing an amount of bone required to be removed from the proximal end of the tibia. Generally speaking, bone is removed from the proximal end of the natural tibia in an amount equaling a height of portions of the tibial component of the artificial knee joint which extend beyond the proximal surface of the tibia after it has been prepared for receiving the tibial component. Typically, regulatory authorities recommend a six millimeter thickness on the insert or other meniscal wear structure, and structural portions of the tibial component need approximately four millimeters for sufficient strength, a full ten millimeters of bone must be removed from the proximal tibia to maintain proper ligament tension and maintain patient leg length. It is desirable to remove as little natural bone as possible, as natural bone is beneficial in many respects and to be preferred over artificial structures to the extent possible.

Prior art attempts have been made to nest the insert into the tibial component somewhat, but only with joints that prevent twisting. See for instance patent to Aubriot (U.S. Pat. No. 5,326,358) and Johnson (U.S. Pat. No. 4,568,348). Accordingly, a need exists for a tibial component of an artificial knee joint which can maintain the regulatory recommended thickness of an insert or other wear structure while minimizing a height of other portions of the tibial component of the artificial knee joint, and still allow twisting, to minimize the amount of required bone removal from the proximal end of the tibia.

SUMMARY OF THE INVENTION

With this invention, an artificial knee joint is provided which includes a femoral component and a tibial component that together satisfy the needs and shortcomings of the prior art identified above. The joint includes a femoral component surgically affixable to a distal end of a femur and a tibial component surgically affixable to a proximal end of a tibia. An insert is also provided as a portion of the tibial component which is removably attachable to the tibial component.

With this invention a jig is also provided to assist in making the cuts necessary to form surfaces on the distal end of the femur appropriate to mate with facets on an internal box face of the femoral component. This jig includes slots or other guides for a cutting tool so that the jig helps the surgeon who is wielding the cutting tool to cut the proper portions of the distal end of the femur away to provide the required surfaces on the distal end of the femur.

The jig is provided to make appropriate cuts for multiple different sizes of femoral components. In particular, slots or other cutting tool guide structures are provided which are the same for each size femoral component to be surgically implanted, except for an anterior surface cut which is made at a variable distance from a posterior surface cut, depending on a size of the femoral component to be implanted. Other slots or other structures within the jig are the same for other cuts to be made to form the surfaces on the distal end of the femur for proper fit with the selected femoral component.

Adjustability of the jig for cutting of the anterior surface is in one embodiment provided by a plurality of separate anterior slots within the jig. In another embodiment, the jig is provided with an anterior slot on a moving portion of the jig that can slide relative to fixed portions of the jig to a desired position for making the necessary cut to form the anterior surface on the distal end of the femur.

The femoral component is generally in the form of a surfacing structure providing a new wear surface on the distal end of the femur. As such it includes a patellar flange portion adapted to be placed adjacent the anterior surface of the distal end of the femur and a medial condylar leg and a lateral condylar leg, both extending down from the patellar flange portion generally parallel to each other. The condylar legs curve posteriorly as they extend from the patellar flange portion.

A distal and posterior face of the femoral component is provided primarily upon the medial condylar leg and lateral condylar leg and is adapted to abut with the insert of the tibial component of the artificial knee joint. The internal box face of the femoral component includes an anterior facet, a distal facet, a posterior facet, and preferably a pair of diagonal facets at either side of the distal facet. The posterior facet is angled back toward a centerline of the femoral component as the posterior facet extends away from the distal facet. Such a negative angle for the posterior facet of the internal box surface and corresponding forming of the posterior surface on the distal end of the femur, allows the distal face of the two condylar legs to wrap around the posterior side of the distal end of the femur sufficiently farther to allow an increase of contact and flexion in operation of the knee joint when compared to prior art knee joint femoral components.

The tibial component includes a substantially planar plate oriented substantially perpendicular to a shaft which is adapted to pass down into a marrow of the tibia and substantially coaxial with a centerline of the tibia. The insert is supported upon a proximal side of the plate. A dovetail rib extends in an anterior to posterior direction from the proximal surface of the plate. The insert includes a dovetail recess sized to be aligned with the dovetail rib on the plate so that the insert can be slid onto the dovetail rib and held tightly to the proximal surface of the plate.

To minimize a thickness of the plate and an overall height of the combination of the insert and the plate, the proximal surface of the plate includes depressions therein and a distal surface of the insert includes lobes therein that drop down into the depressions in the proximal surface of the plate. In this way, a maximum thickness of the insert is maintained, especially beneath wells in a proximal surface of the insert, without adding height to the overall insert and plate of the tibial component.

Two wells in the proximal surface of the insert have a curvature matching a curvature of the condylar legs of the femoral component. Thus, the condylar legs of the femoral component can reside within these generally spherical wells in the insert and the joint can experience flexion while maintaining surface contact between the wells of the insert and the condylar legs of the femoral component.

The wells have valleys that extend arcuately and mostly in an anterior direction away from low points of the wells. These valleys are of lesser depth in a distal direction as the valleys extend anteriorly away from low points of the wells. The valleys curve about a center point axis aligned with the low point of the other of the pair of wells. Side walls of the valleys are appropriately gradual so that cross-sections of the valleys perpendicular to centerlines of the valleys contain a curvature similar to that of the condylar legs of the femoral component. In this way, one of the condylar legs can remain at a low point within one of the wells while the other condylar leg can rotate along a valley of one of the wells away from the low point and moving slightly upwardly in a proximal direction. As the elevation of the valleys increase, tension on ligaments and muscles of the knee joint tighten to resist further pivoting rotation of the knee joint. Gravity loads tend to encourage the condylar legs back to the low points of the wells, as well as forces applied by the ligaments and muscles themselves. Such pivoting rotation can occur in either direction with one of the condylar legs remaining in a low point of one of the wells while the other condylar leg can move arcuately within its well. In this way, a small amount of knee pivoting rotation action is provided by the artificial knee joint of this invention, mimicking performance of a natural knee joint being replaced.

OBJECTS OF THE INVENTION

Accordingly, a primary object of the present invention is to provide an artificial knee joint which mimics as closely as possible the function of a natural knee joint.

Another object of the present invention is to provide an artificial knee joint which is easy for a surgeon to size and install properly.

Another object of the present invention is to provide a method and system for preparing a distal end of a femur for receipt of a femoral component of an artificial knee joint which is easy to perform and similar for many different sizes of artificial knee joint components.

Another object of the present invention is to provide an artificial knee joint sizing system which has multiple different size components therein but which maintain similar size for many portions thereof to simplify the forming of cuts necessary to shape the distal end of the femur.

Another object of the present invention is to provide a single tool for shaping a distal end of the femur to receive a femoral component of an artificial knee joint which can properly shape the distal end of the femur for a variety of different sizes of femoral components.

Another object of the present invention is to provide an artificial knee joint which requires a minimal amount of bone removal from the proximal end of a tibia for receipt of a tibial component of the artificial knee joint.

Another object of the present invention is to provide an artificial knee joint which facilitates pivoting rotation in both a clockwise and counterclockwise direction.

Another object of the present invention is to provide an artificial knee joint which includes many portions thereof which are symmetrical and usable for either a left or right knee.

Another object of the present invention is to provide an artificial knee joint which provides a greater amount of contact between condyles and increase flexion within the artificial knee joint.

Another object of the present invention is to provide an artificial knee joint which includes a set of femoral components of different sizes for different sized femurs, with each of the components in the set having many surfaces which share a common size and shape, to simplify the different cuts required on the distal end of the femur for receipt of the femoral component thereon.

Another object of the present invention is to provide an artificial knee joint with a tibial insert for an artificial knee joint which is formed of a meniscus material that is available for wear that exhibits a low profile such that a minimum amount of natural tibia bone is required to be removed.

Other further objects of the present invention will become apparent from a careful reading of the included drawing figures, the claims and detailed description of the invention.

BRIEF DESCRIPTION OF THE DRAWINGS

FIGS. 3 and 4 are perspective views of an adjustable jig attachable to the distal surface of the femur similar to the fixed jig of FIG. 2, but which adjustable jig features an adjustable portion for moving one of the slots to different distances adjustably spaced from other slots within fixed portions of the jig.

FIG. 5 is a side elevation view similar to that which is shown in FIG. 2, but illustrating use of the adjustable jig of FIGS. 3 and 4 thereon.

FIG. 29 is a perspective view of an alternative tibial component with an augment removably attachable thereto and shown exploded away from the tibial component and with a second position for the augment shown in broken lines.

FIG. 30 is a perspective view of the alternative tibial component of FIG. 29 with the augment attached to the tibial component.

FIG. 31 is a full sectional view of the alternative tibial component and augment taken along line 31-31 of FIG. 30.

DESCRIPTION OF THE PREFERRED EMBODIMENT

Figure 1:
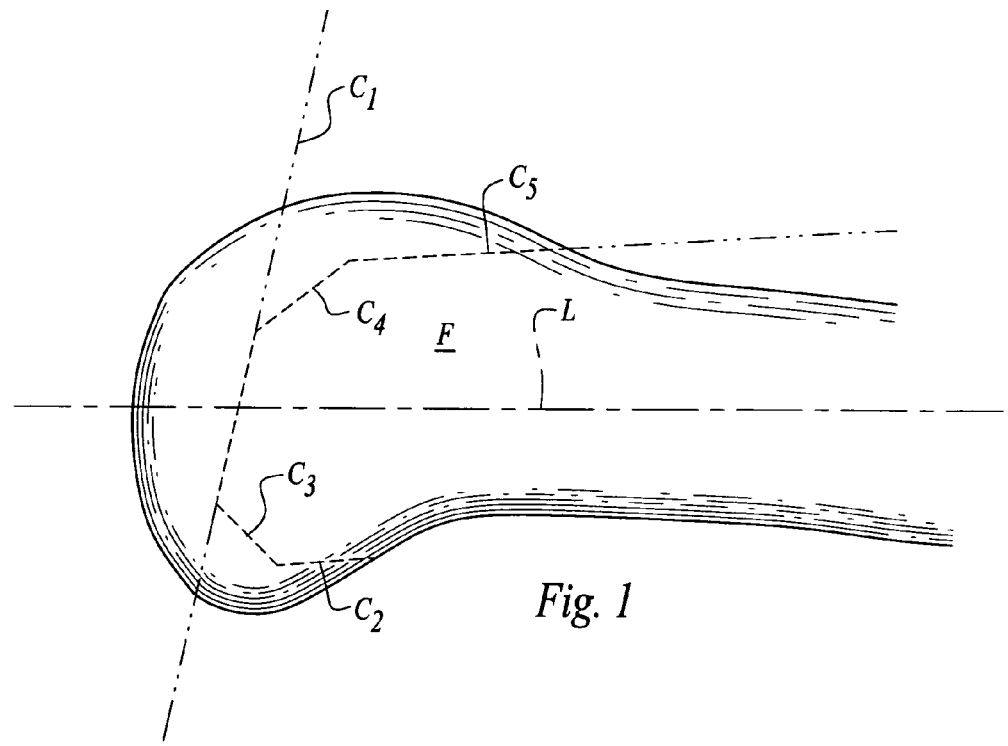
FIG. 1 is a side elevation view of a distal end of a femur before cuts are made thereto to form surfaces on the distal end of the femur for receipt of the femoral component of the artificial knee joint, and with cut lines to be made shown in broken lines thereon.

Referring to the drawings, wherein like reference numerals represent like parts throughout the various drawing figures, reference numeral 10 is directed to an artificial knee joint for replacing a natural knee joint between a femur F and a tibia T. The invention includes a femoral component 20 and a tibial component 40, as well as tools 2, 12 for forming a distal end of the femur F to receive the femoral component 20. The invention also includes methods for preparing the distal end of the femur to receive an appropriately sized femoral component.

Figure 15:
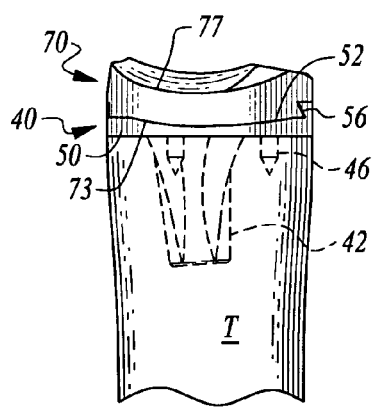
FIG. 15 is a side elevation view of the tibial component shown in place upon the proximal end of the tibia.
Figure 16:
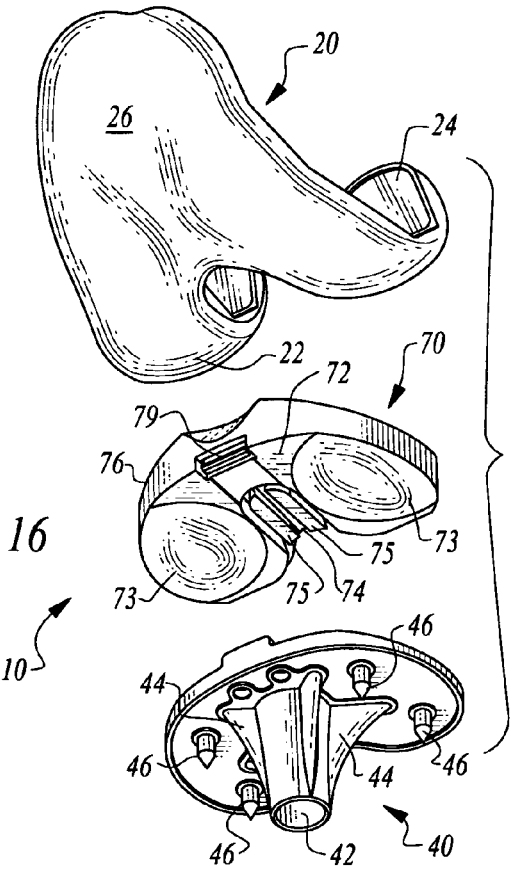
FIG. 16 is an exploded parts view of the entire artificial knee joint shown in perspective and from below.
Figure 17:
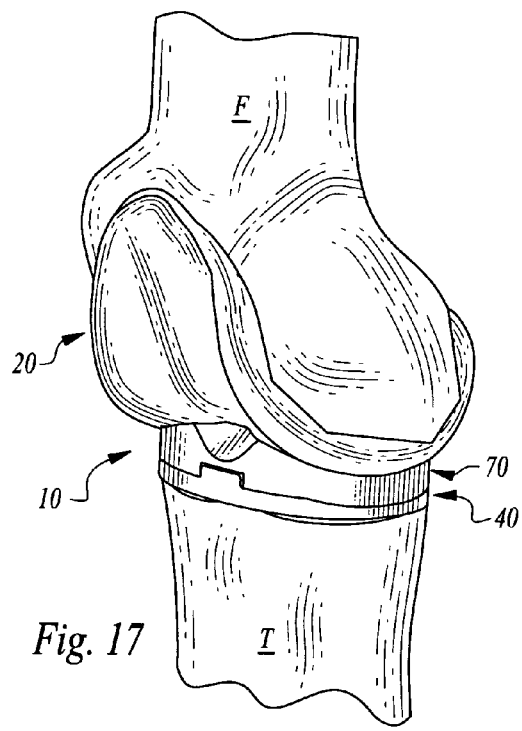
FIG. 17 is a perspective view of the completed artificial knee joint in extension and with the femur and tibia brought together.
Figure 18:
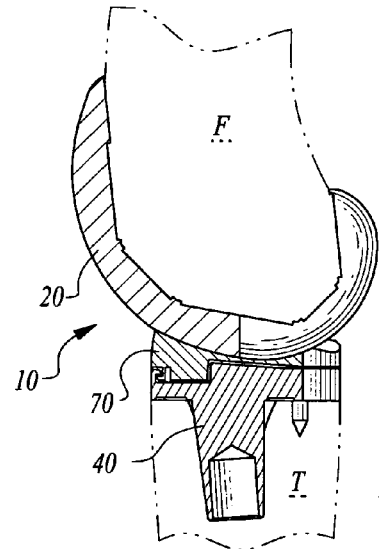
FIG. 18 is a sectional side elevation view of that which is shown in FIG. 17.
Figure 19:
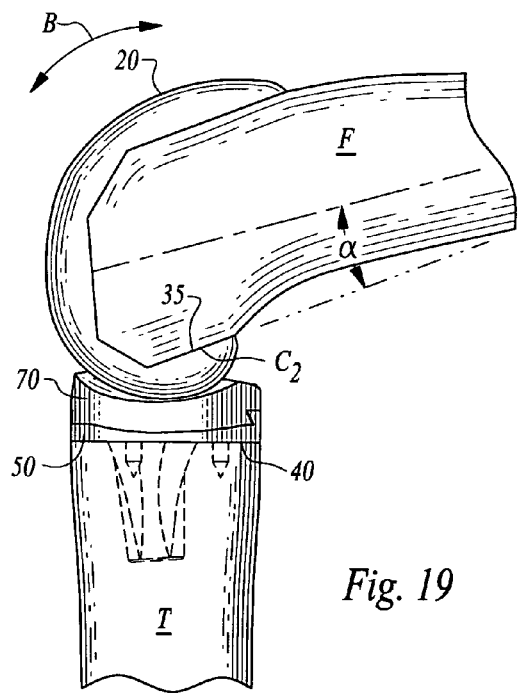
FIG. 19 is a side elevation view of that which is shown in FIG. 17, and with a knee joint in a state of partial flexion.
Figure 20:
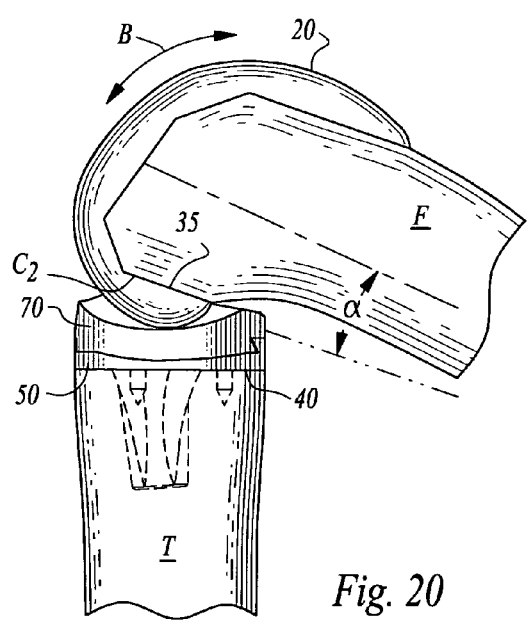
FIG. 20 is a side elevation view similar to FIG. 19, but showing full flexion of the knee joint.

In essence, and with particular reference to FIGS. 15 and 16, the basic details of the artificial knee joint 10 are described, according to a preferred embodiment. The joint 10 includes the femoral component 20 adapted to be coupled to an appropriately shaped distal end of the femur F. The joint 10 also includes a tibial component 40. The tibial component 40 primarily includes a shaft 42 for insertion into the proximal end of the tibial T and a plate 50 of generally planar form perpendicular to the shaft 42. An insert 70 provides a removable portion of the tibial component 40 which attaches to the plate 50. This insert 70 cooperates with a dovetail rib 60 on the plate 50 to secure the insert 70 tightly to the plate 50. The insert 70 can then act somewhat as a meniscal component within the joint 10 for interfacing with the femoral component 20 in an articulating fashion during operation of the joint 10 (FIGS. 18-20).

Figure 2:
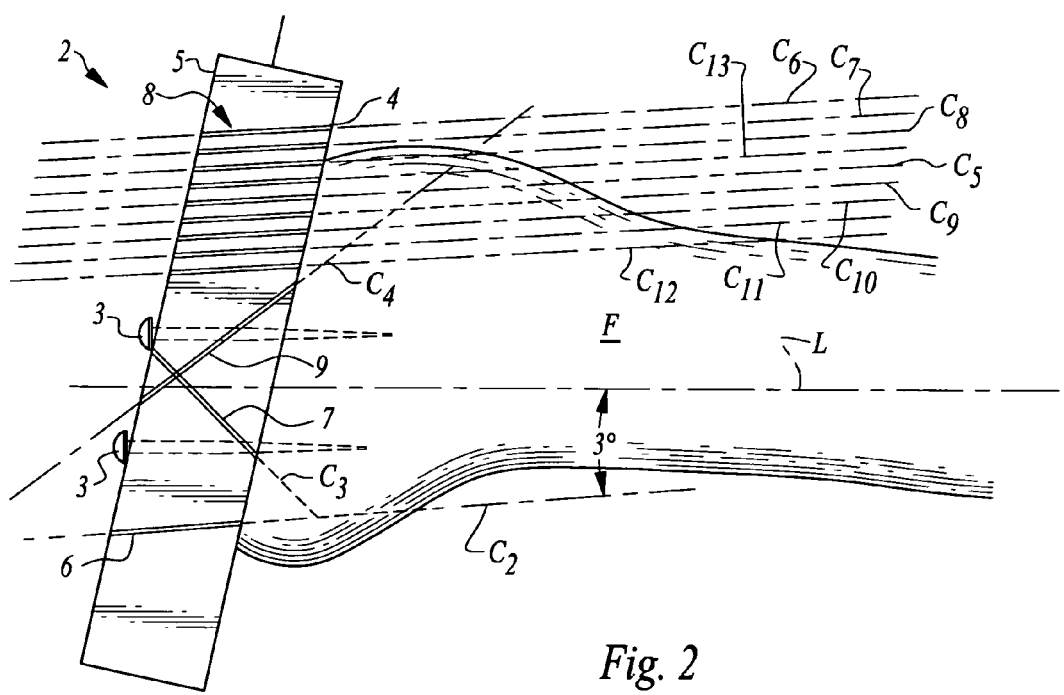
FIG. 2 is a side elevation view similar to that which is shown in FIG. 1, but after making a first cut to the femur to form the distal surface of the femur, and after attachment of a fixed jig to the distal surface for guiding of cutting tools for the making of other cuts to form other surfaces on the distal end of the femur.
Figure 6:
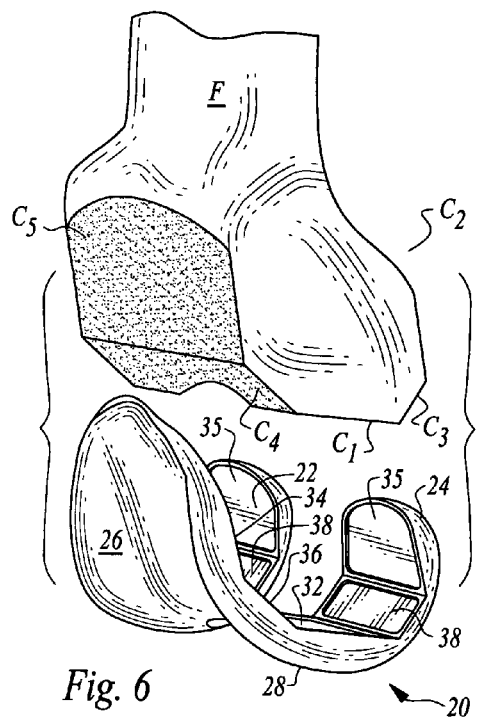
FIG. 6 is a perspective view of the distal end of the femur with a femoral component of the artificial knee joint exploded therefrom, and illustrating how the femoral component is oriented and configured to fit upon the distal end of the femur.

More specifically, and with particular reference to FIGS. 1-5, details of jigs 2, 12 for use in forming surfaces of the distal end of the femur F to receive the femoral component 20, are described according to a preferred embodiment. Before using either of the jigs 2, 12, a cut $C_1$ is made to the distal end of the femur (FIG. 1). This cut is typically approximately perpendicular to the centerline L of the femur F, but most preferably slightly angled, as shown in FIG. 1. The fixed jig 2 provides one form of tool for assisting a surgeon in properly forming surfaces on the distal end of the femur F to receive the femoral component 20. The fixed jig 2 is generally in the form of a thick rigid structure which has an abutting face 4 which is caused to abut a distal surface of the femur F formed by cut line $C_1$ (FIGS. 1 and 2). Pins or pegs 3 provide one form of means to temporarily secure the fixed jig 2 to the distal surface of the femur F.

The fixed jig 2 includes a face 5 opposite the abutting surface 4. Slots pass from the face 5 to the abutting surface 4 for guiding of a cutting tool through the fixed jig 2, then into bone of the femur F to form the surfaces required on the distal end of the femur F to receive the femoral component 20. In particular, a posterior slot 6 is provided passing from the face 5 through to the abutting surface 4. This posterior slot 6 is utilized to form cut $C_2$ (FIGS. 1 and 2). Diagonal slots 7, 9 are separately utilized to form cuts $C_3$ and $C_4$.

Figure 12:
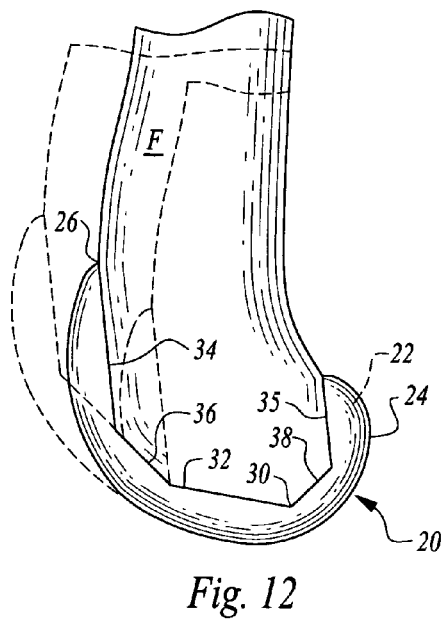
FIG. 12 is a side elevation view of that which is shown in FIG. 8, and illustrating in broken lines how two other femoral components of larger and smaller sizes share common surfaces with each other, except for an anterior facet and portions of a distal face of the femoral component to allow for simple size adjustability. This view also shows the femurs of different sizes matching those of the femoral components.
Figure 11:
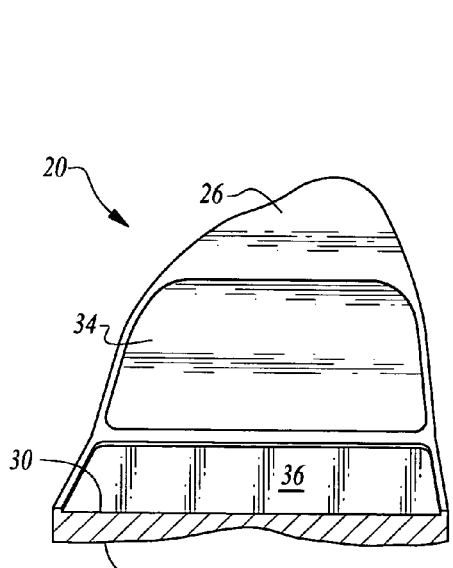
FIG. 11 is a rear sectional view of that which is shown in FIG. 8.
Figure 13:
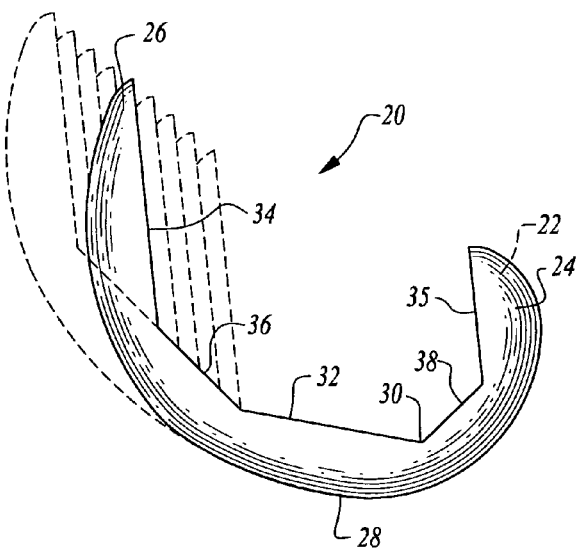
FIG. 13 is a side elevation view of that which is shown in FIG. 12 without the femurs shown and depicting nine sizes of femoral components and how they relate together.
Figure 14:
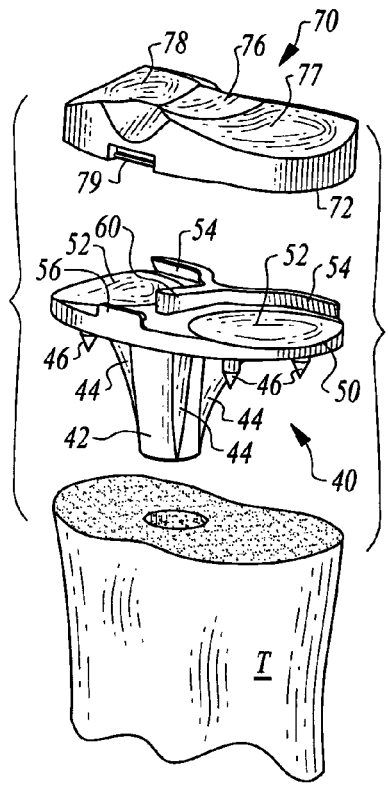
FIG. 14 is an exploded parts view of a tibial component of the artificial knee joint of this invention showing an insert portion of the tibial component exploded away from a plate and shaft portion of the tibial component, and exploded from a proximal end of a tibia.

The fixed jig 2 also includes an anterior slot array 8 aligned with cut lines $C_5$-$C_{13}$. In this embodiment nine separate anterior slots are provided within the slot array 8. Each separate slot corresponds with one particular size for the femoral component 20 (FIG. 12). The surgeon makes a determination as to which femoral component 20 would best be utilized with the patient. The surgeon then makes one cut through one of the anterior slots in the anterior slot array 8 to form the surface corresponding with cut $C_5$ (FIG. 1) or one of the other cut lines $C_6$-$C_{13}$ (FIG. 2) to form the anterior surface of the distal end of the femur F as desired to fit with the femoral component 20 that has been selected.

An adjustable jig 12 provides an alternative to the fixed jig 2. The adjustable jig 12 (FIGS. 3-5) is generally similar to the fixed jig 2 except where particularly described herein. An abutting surface 14 is thus provided for temporary attachment adjacent to the distal end of the femur F formed by cut line $C_1$ (FIG. 1). Once the adjustable jig 12 is attached to the distal end of the femur F, a guide 13 is utilized which slides (along arrow A of FIG. 5) relative to other portions of the adjustable jig 12 that are fixed to the femur F. When the guide 13 is touching the femur F, an adjustable slot 16 is positioned where desired for forming of a cut to form the anterior surface of the femur F.

This guide 13 is coupled to a structure in which the adjustable slot 16 is formed, along with a mast 17. The mast 17 is adapted to slide within a groove 18 formed in fixed portions of the adjustable jig 12. A cross-sectional contour of the mast 17 and groove 18 are preferably selected to prevent rotation of the mast 17 within the groove 18, such as a "cross" form (FIG. 3). Thus, the guide 13 and adjusting slot 16 can slide relative to other slots within the adjustable jig 12 to place the adjustable slot 16 where desired to form the cut associated with the anterior surface for the distal end of the femur F.

Most preferably, the face 15 of the adjustable jig 12 includes a set line 19 thereon and the mast 17 includes a series of numbers and associated graduation marks thereon. These indicia and graduation marks could be placed on the face 15 with the set line 19 formed on the mast 17 if desired. When the guide 13 abuts the femur F (FIG. 5) a user can see which graduation adjacent which indicia is aligned with the set line 19 (FIG. 4). This indicia, such as a number or letter, corresponds with the size of femoral component (FIG. 12) that will properly fit upon the distal end of the femur F after making cuts through the various slots of the adjustable jig 12.

Utilizing one of the jigs 2, 12 of this invention, each of the surfaces of the distal end of the femur are formed to have a similar size, shape and relative orientation to other surfaces on the distal end of the femur, with the exception of the anterior surface. This anterior surface maintains the same orientation relative to other surfaces on the distal end of the femur, but exhibits a variable distance away from the posterior surface of the distal end of the femur. Thus, each femoral component 20 within a set of femoral components 20 of different sizes (FIG. 12) can be similar in size and shape, except for portions which are to be located adjacent the anterior surface of the distal end of the femur. Such anterior portions of the femoral component 20 are each slightly modified for different sizes within the set of femoral components. To achieve this similarity between femoral components of different sizes, one of the diagonal cuts exhibits variable length, with this anterior diagonal cut being almost non-existent for the smallest femur F, and largest to accommodate the largest femurs F.

In addition, the femoral component 20, while it could be made generic and suitable for use on either a left or right knee, is most preferably optimized to be slightly asymmetrical to be provided either on a left knee or a right knee implantation site. Thus, overall a surgeon need only have one jig, one cutting tool for use with the jig and one set of femoral components associated with the left or right knee that is receiving the artificial knee joint. Simplicity and freedom from potential error results from such a simplified system.

With particular reference to FIGS. 6-17, details of the femoral component 20 of the artificial knee joint 10 are described, according to a preferred embodiment. These details are described with regard to a femoral component 20 of midsize (FIG. 12), with details of other femoral components 20 within a set of different sizes of femoral components 20 being similar, except for size adjustability as depicted in FIG. 12.

The femoral component 20 generally includes a medial condylar leg 22 and a lateral condylar leg 24 which each extent from a patellar flange portion 26. Legs 22, 24 exhibit a curvature which allow them to wrap around the distal end of the femur F from the anterior surface to the posterior surface and over the distal surface of the femur F. A distal face 28 of the femoral component 20 is a generally curving surface optimized to abut and articulate against the insert 70 of the tibial component 40 described in detail below. Each condylar leg 22, 24 has a separate (same) curvature on the distal face 28 which is preferably substantially spherical, and most importantly has a curvature which matches that of the wells 77, 78 on the proximal surface 76 of the insert 70, described in detail below.

An internal box face 30 defines that portion of the femoral component 20 which abuts against the distal end of the femur F. This internal box face 30 is divided into separate facets to which an adhesion medium can engage, or other fastening structures can be connected. The internal box face 30 includes a distal facet 32 which is close to perpendicular to a centerline of the femoral component 20, with a centerline of the femoral component 20 defined as a line aligned with a centerline of the femur F when the femoral component 20 is attached to the distal end of the femur F. However, the distal facet 32 preferably extends slightly further distally on a side of the distal facet 32 closest to the posterior diagonal facet 38. The distal facet 32 can support an axial structure which can penetrate into the femur F, or other attachment structures can be provided to extend generally proximally into the femur F. The distal facet 32 preferably maintains its size and shape for all sizes of femoral components 20.

The distal facet 32 is preferably substantially planar, but could have a differing contour provided that the distal surface of the distal end of the femur F is similarly formed. Because planar surfaces are most easily formed on the distal end of the femur F, the internal box face 30 of the femoral component 20 is similarly formed with planar facets such as the distal facet 32.

An anterior face 34 defines a portion of the internal box face 30 of the femoral component 20 adapted to abut against the anterior surface of the distal end of the femur F. A posterior facet 35 is similarly adapted to abut the posterior surface of the distal end of the femur F. An anterior diagonal facet 36 extends diagonally between the distal facet 32 and the anterior facet 34. This anterior diagonal facet 36 is of varying size depending on which femoral component 20 size is involved. A posterior diagonal facet 38 extends between the posterior facet 35 and the distal facet 32.

Figure 8:
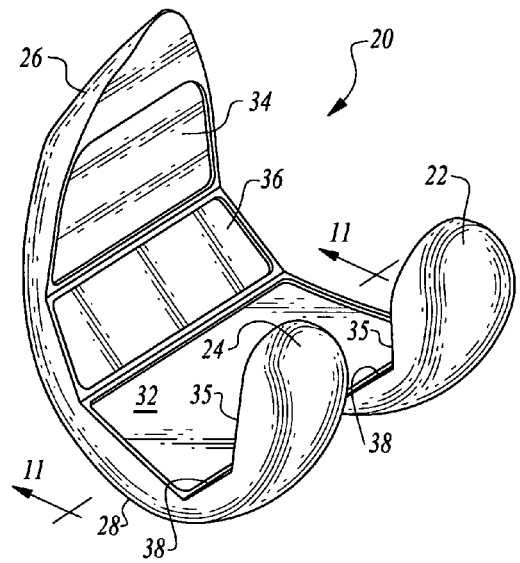
FIG. 8 is a perspective view of the femoral component of FIGS. 6 and 7.
Figure 7:
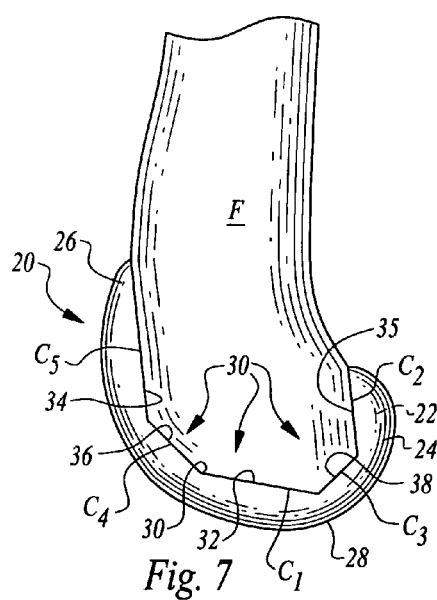
FIG. 7 is a side elevation view of the distal end of the femur including a femoral component attached thereto.
Figure 9:
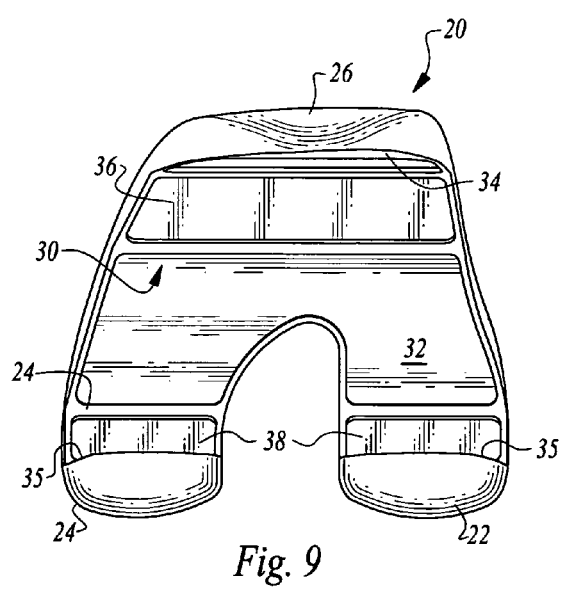
FIG. 9 is a top plan view of that which is shown in FIG. 8.
Figure 10:
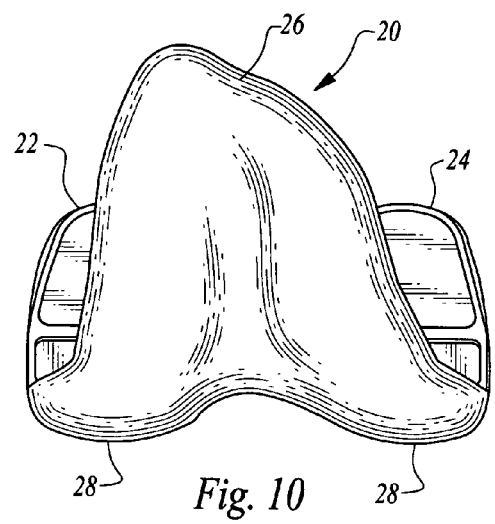
FIG. 10 is a front elevation view of that which is shown in FIG. 8.

Each of these facets 32, 34, 35, 36, 38 are preferably each planar and joined to adjacent facets 32, 34, 35, 36, 38 along transition lines which are linear in form and extend laterally an entire width of the internal box face 30 of the femoral component 20 (FIG. 8). Most preferably, these transition lines include ribs thereon with other portions of the facets 32, 34, 35, 36, 38 away from these transition lines recessed slightly. Side edges of the internal box face 30 can also be raised slightly. Such ribs are depicted in FIGS. 6, 8-11 and 17, but could have a variety of different configurations or could be omitted altogether. Recesses between the ribs provide a region for adhesive or bone in-growth medial to help adhere the femoral component 20 to the femur F.

Importantly, the posterior facet 35 has a negative angle $\alpha$ (FIGS. 2 and 19) relative to a centerline of the femoral component 20 and a centerline of the femur F when attached to the femur F. As best depicted in FIG. 18, this negative angle $\alpha$ is most preferably approximately 3°, but could be increased or decreased to optimize the design. Prior art femoral components of artificial knee joints are not known to have such a negative angle. By providing such a negative angle, a greater amount of flexion and contact can be obtained (along arrow B of FIG. 18) between the tibia T and femur F.

Cut line $C_2$ associated with posterior slot 6 in the fixed jig 2 (FIG. 2) provides the internal box surface of the distal end of the femur F with a negative angle relative to a centerline of the femur F which corresponds with the negative angle of the posterior facet 35 relative to a centerline of the femoral component 20 (FIG. 18).

Note that this posterior facet 35 is in fact a pair of separate facets with each facet on one of the condylar legs 22, 24. Also, the posterior diagonal facet 38 is actually split between the two condylar legs 22, 24 and the distal facet 32 extends partially onto each of the legs 22, 24. As these split facets 32, 35, 38 are coplanar, they are often referred to as a single plane and a single facet for simplification.

The anterior diagonal facet 36 maintains a common position for each size of femoral component 20 (FIG. 12. However, this facet 36 varies in length to accommodate anterior facets 34 of different positions for the different femoral component sizes. For a smallest size, this anterior diagonal facet 36 is reduced to zero or near zero length so that the anterior facet is directly or almost directly adjacent the distal facet 32. Other facets preferably maintain their size and relative orientation for the different sized femoral components 20.

With particular reference to FIGS. 13-26, details of the tibial component 40 are described, according to a preferred embodiment. The tibial component 40 is preferably formed as a rigid construct from high strength material such as titanium or cobalt chrome. The tibial component includes a shaft 42 of elongate form adapted to be aligned with a centerline of the tibia T and to be driven down into a marrow space within the tibia T. This shaft 42 extends down from a plate 50 which is generally planar and oriented generally perpendicular to the shaft 42. The plate 50 is adapted to abut the proximal surface of the tibia T. Gussets 44 are formed on sides of the shaft 42 and generally become thicker as the gussets 44 extend proximally toward the plate 50. These gussets 44 help to give additional strength to the plate 50 and to the shaft 42, and also to further assist the shaft 42 and tibial component 40 overall in being securely affixed to the tibia T. Furthermore, prongs 46 preferably extend distally from the plate 50 to further engage the proximal end of the tibia T.

Figures 21, 22:
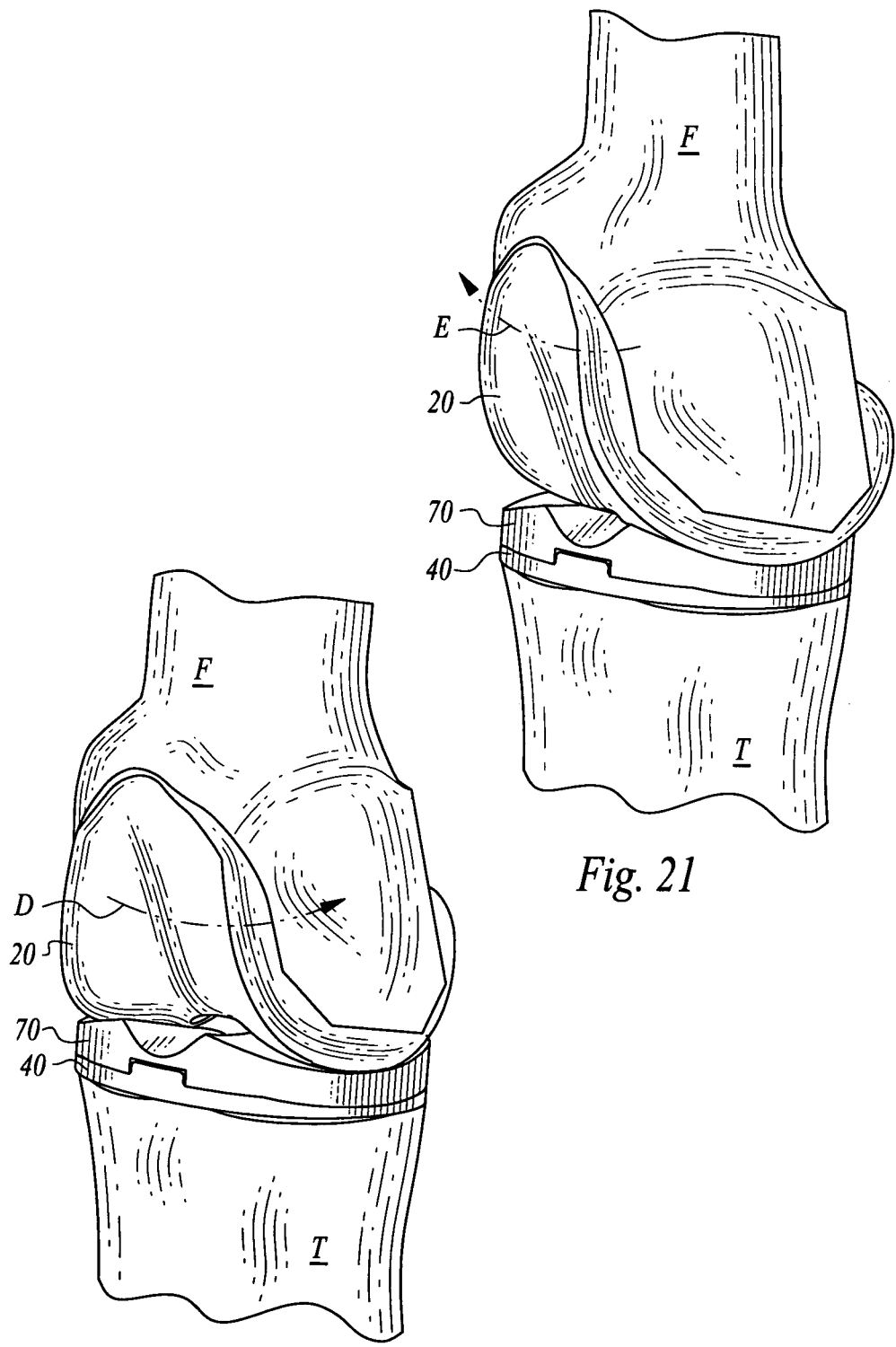
FIGS. 21 and 22 are perspective views similar to that which is shown in FIG. 17, but illustrating pivoting rotation of the knee joint in both a clockwise and counterclockwise direction.

The plate 50 is generally oval shaped and is perhaps best seen in FIG. 22. The plate 50 includes a pair of spherical depressions 52 on either side of a dovetail rib 60 passing medially between the spherical depressions 52. The spherical depressions 52 need not necessarily be spherical, but could have some other contour. These depressions 52 extend distally down into the plate 50 and help to make the tibial component 40 exhibit an overall lesser distal height to minimize an amount of bone required to be removed from the tibia T.

The plate 50 includes a posterior wall 54 extending up from a posterior edge of the plate 50. An anterior tab 56 also extends up from the plate 50 near a lateral midpoint of the anterior edge of the plate 50. A tooth 58 extends posteriorly from the anterior tab 56. The tab 56 helps to hold the insert 70 onto the plate 50, as described in detail below. Most preferably the posterior wall 54 exhibits an overhang that extends anteriorly to some extent. This overhang helps the posterior wall 54 to hold the insert 70 securely adjacent the plate 50, as described in detail below.

The dovetail rib 60 extends proximally up from a midportion of the plate 50. This dovetail rib 60 is elongate in form extending from an anterior end 62 to a posterior end 64. The anterior end 62 stops short of the anterior tab 56, so that a gap exists between the anterior tab 56 and the anterior end 62 of the dovetail rib 60. The posterior end 64 of the dovetail rib 60 is preferably joined with the posterior wall 54 extending up from the proximal surface of the plate 50.

Figure 23:
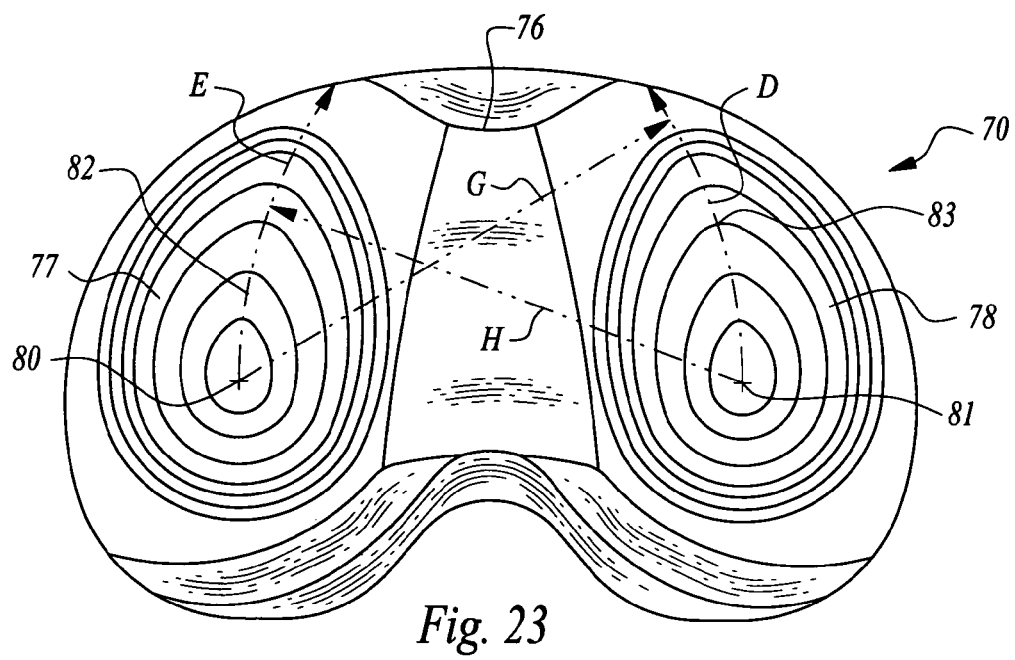
FIG. 23 is a top plan view of the insert of the tibial component of this invention.
Figure 24:
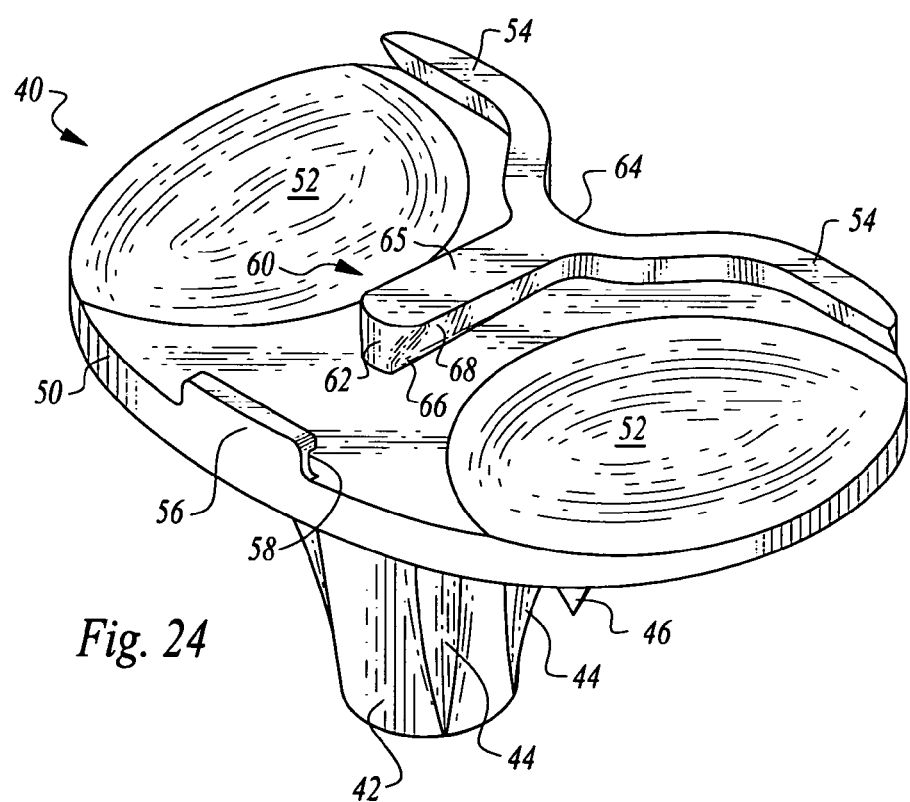
FIG. 24 is a perspective view of the plate and shaft of the tibial component of this invention.
Figure 25:
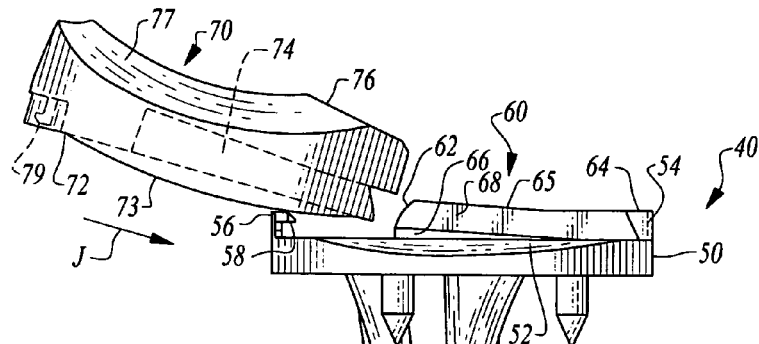
FIG. 25 is a side elevation view of the tibial component showing the insert portion in the process of being slid onto the plate.
Figure 26:
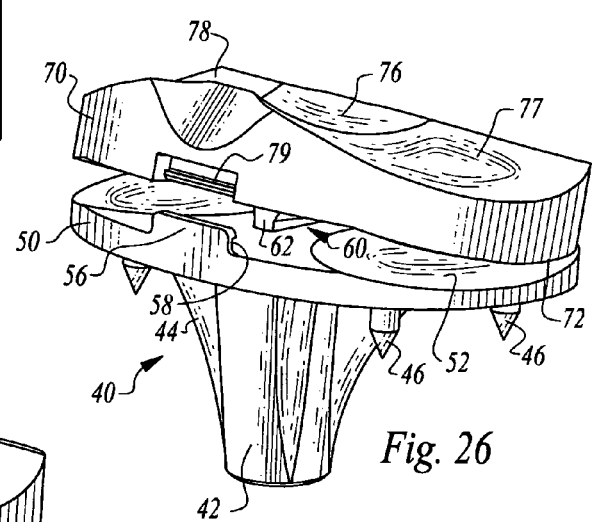
FIG. 26 is a perspective view similar to that which is shown in FIG. 25 but after the insert has been almost fully attached to the plate of the tibial component.
Figure 27:
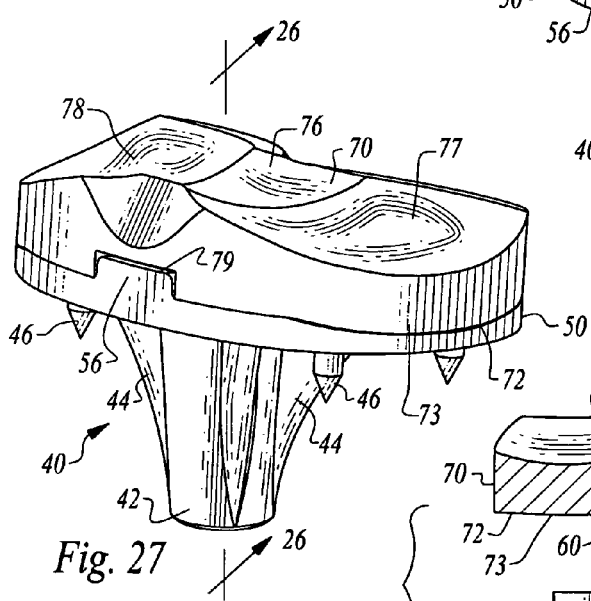
FIG. 27 is a perspective view similar to that which is shown in FIG. 26, but after the insert has been completely attached to the plate of the tibial component.
Figure 28:
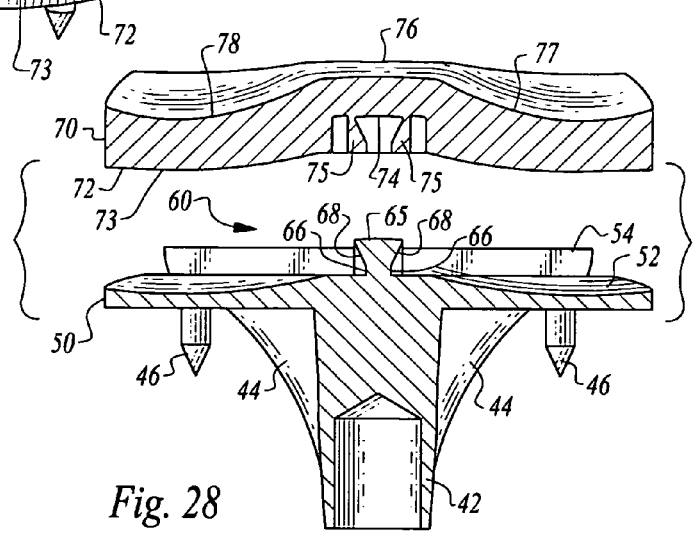
FIG. 28 is a full sectional elevation view of the tibial component including the insert portion and the plate and shaft portion, with the insert portion exploded away from other portions of the tibial component to most clearly show complementally formed contours thereof.

The dovetail rib 60 includes a pair of substantially parallel side walls 66 adjacent to the proximal surface of the plate 50 and forming a lower portion of the dovetail rib 60 joining the dovetail rib 60 to the plate 50 (FIGS. 23 and 26). A top wall 65 defines a portion of the dovetail rib 60 extending most proximally from the plate 50. The top wall 65 exhibits a taper in a distal and posterior direction from the anterior end 62 toward the posterior end 64.

Beveled walls 68 extend up from the side walls 66 to the top wall 65. These beveled walls 68 provide the dovetail rib 60 with its dovetail cross-section. The beveled walls 68 preferably maintain their form from the anterior end 62 to the posterior end 64. The side walls 66 preferably taper in height from a greatest height adjacent the anterior end 62 to a least proximal height adjacent the posterior end 64, where most preferably the side walls 66 merge into the proximal surface of the plate 50, so that adjacent the posterior end 64, the dovetail rib 60 is formed of only the beveled wall 68, without the side walls 66. This tapering of the dovetail rib 60 causes a wedging action with the dovetail recess 74 of the insert 70 when the insert 70 is slid onto the dovetail rib 60 (along arrow J of FIG. 25).

Most preferably, the entire dovetail rib 60, anterior tab 56, posterior wall 54, plate 50, shaft 42 and prongs 46 are formed together as a unitary monolithic mass of a common material. Such forming could be by molding, machining or some combination of procedures. As an alternative, various separate parts of the tibial component 40 could be attached together, such as by welding or other bonding, or through utilization of appropriate biocompatible fasteners.

The tibial component 40 also can be considered to include the insert 70 as a separately attachable portion thereof. Within the artificial knee joint 10, the insert 70 moves along with the plate 50 and shaft 40 as a single structure. However, the insert 70 can be removably attached from and to other portions of the tibial component 40. Also, the insert 70 is typically formed of a more resilient material than that forming other portions of the tibial component 40, and particularly the plate 50 and shaft 42. For instance, the insert 70 could be formed of a biocompatible polymeric hydrocarbon material which has some degree of resilience and flexibility to best accommodate loads associated with the femoral component 20 pressing down on the insert 70 in a distal direction.

The insert 70 is itself a monolithic structure formed such as by molding or machining to have the contours shown in FIGS. 13-21 and 23-26. The insert 70 includes a distal surface 72 adapted to abut the plate 50. Spherical lobes 73 extend down from the distal surface 72 to reside within the spherical depressions 52 in the plate 50. These spherical lobes 73 could be a different shape, particularly if the depressions 52 are a shape different than spherical. Also, while the lobes 73 preferably fill the depressions 52, they could be smaller than or a different shape than the depressions 52.

The distal surface 72 of the insert 70 also includes a dovetail recess 74 therein. This dovetail recess 74 is interposed between engagement bars 75. The dovetail recess 74 has a contour similar to that of the dovetail rib 60. Thus, the insert 70 can have its dovetail recess 74 slid onto the dovetail rib 60 (arrow J of FIG. 23) to attach the insert 70 to the plate 50.

The insert 70 includes a proximal surface 76 opposite the distal surface 72. The proximal surface 76 is adapted to support the femoral component 20 or other femoral structures thereon. For instance, it is conceivable that the femur F might not be modified, but impact directly upon the proximal surface 76 of the insert 70, or that some other form of interface besides the femoral component 70 might be utilized. The proximal surface 76 is perhaps best seen in FIG. 21. A left well 77 and right well 78 extend distally down into the proximal surface 76. A recess 79 is formed on an anterior portion of the insert 70. This recess 79 is sized to receive the tab 56 and tooth 58 therein to lock the insert 70 to the plate 50 most securely.

The wells 77, 78 exhibit a particular contour to allow both flexion of the femoral component 20 relative to the tibial component 40, and also a degree of pivoting rotation (about arrows D and E of FIGS. 19 and 20) in both a clockwise and counterclockwise direction. In particular, the wells 77, 78 include low points 80, 81 that define most distal portions of the wells 77, 78. Side walls of the wells 77, 78 near these low points 80, 81 are preferably substantially spherical in form matching a radius of curvature of the condylar legs 22, 24 of the femoral component 20. If these condylar legs 22, 24 exhibit a contour other than spherical, most preferably surfaces of the wells 77, 78 adjacent the low points 80, 81 would be appropriately modified to match such curvature.

By matching this curvature, surface contact is provided between the wells 77, 78 and the condylar legs 22, 24. Thus, both gravity forces and forces applied by muscles and tendons will tend to cause the condylar legs 22, 24 to remain within the wells 77, 78 adjacent the low points 80, 81 thereof. Such positioning will be maintained during flexion (rotation along arrow B of FIG. 18). However, if pivoting rotating loads are applied (such as along arrows D and E of FIGS. 19 and 20) such pivoting rotation is accommodated.

In particular, if the medial condylar leg 22 is located within the right well 78 and the lateral condylar leg 24 is located within the left well 77, before pivoting rotation action, the medial condylar leg 22 will be aligned with the low point 81 and the lateral condylar leg 24 will be aligned with the low point 80. For pivoting rotation in a clockwise direction, the medial condylar leg 22 will remain at the low point 81. However, the lateral condylar leg 24 will rotate along arrow E (FIGS. 19 and 21) along a left valley 82 within the left well 77 in a generally anterior direction, but following an arc maintaining a constant distance from the low point 81 of the right well 78, depicted by arrow H (FIG. 21).

Alternatively, if pivoting rotation is required in a counterclockwise direction, the lateral condylar leg 24 will remain within the low point 80 of the left well 77 and the medial condylar leg 22 within the right well 78 will move out of the low point 81 and along the right valley 83 along arrow D (FIGS. 20 and 21). This right valley 83 is defined by a constant distance away from the low point 80 of the left well 77 depicted by arrow G (FIG. 21).

The valleys 82, 83 slope proximally away from the low points 80, 81 slightly. Thus, as such pivoting rotation action occurs, the condylar legs 22, 24 are moving anteriorly and proximally along the valleys 82, 83. This adds tension to the ligaments and muscles around the knee joint 10 and require work against gravity. Preferably, the slope of the valleys 82, 83 away from the low points 80, 81 rather significantly increases in slope near an end point of the valleys 82, 83 most distant from the low points 80, 81. Thus, the legs 22, 24 would need to move proximally at a significantly more rapid rate as a greater amount of pivoting rotation is encountered. Knee ligaments and muscles, as well as gravity resist such further pivoting rotation, such that the knee has stability against excessive pivoting rotation.

While the condylar legs 22, 24 and the wells 77, 78 enjoy surface contact over at least portions thereof before such pivoting rotation occurs, such surface contact is maintained even during pivoting rotation for the one condylar leg 22, 24 which remains stationary within the low point 80, 81. For the other condylar leg 24, 22, that is moving along a valley 82, 83 within one of the wells 77, 78, contours of side walls of the wells 77, 78 on either side of the valleys 82, 83 are configured with a cross-section perpendicular to a centerline of the valleys 82, 83 which matches a cross-section of the condylar legs 22, 24. Thus, contact is maintained for the legs 22, 24 moving within the valley 82, 83 away from the low point 80, 81. Thus, point loads are avoided even during such pivoting rotation motion. By distributing loads and avoiding point loading, but rather either line loading or surface loading, a rate of wear and stress upon the insert 70 and the femoral component 20 is minimized.

Additionally, because the wells 77, 78 extend down into the proximal surface 76 of the insert 70, and because regulatory agencies typically recommend a minimum amount of wear height within the insert 70 or other meniscal structure, having a flat distal surface 72 on the insert 70 would require the insert 70 to exhibit a greater height similar to a depth of the wells 77, 78 than if the wells were not there. For instance, it is recommended that if a minimum of six millimeters must be maintained within the insert 70, upon implantation, and if the wells 77, 78 have three millimeters of distal depth, the proximal surface 76 of the insert 70 must be at least nine millimeters away from the distal surface 72.

By providing spherical lobes 73 on the distal surface 72 of the insert 70, such as three millimeters thick, and similar depressions 52 in the plate 50, the required thickness for the insert 70 can be maintained (i.e. six millimeters) without requiring a perimeter distance between the distal surface 72 and proximal surface 76 to be increased. Rather, thickness is maintained while shortening an overall height of the tibial component 40 of the joint 10.

Because the depressions 52 in the plate 50 reduce the strength of the plate 50 somewhat, the gussets 44 are provided to maintain sufficient plate 50 strength. In particular, the gussets 44 preferably are generally triangularly shaped planar structures oriented in substantially vertical planes radiating from the shaft 42. Preferably, four gussets 44 are provided with a widest portion of each gusset 44 adjacent the underside of the plate 50 and narrowing down to the tip of the shaft 42 most distant from the plate 50. Also, prongs 46 extend down substantially vertically from the underside of the plate 50 at locations spaced from the shaft 42. Preferably, four such prongs 46 are provided with a length of about a fourth that of the shaft 42. Overall, such nesting of a portion of the insert 70 within a portion of the plate 50 can provide up to a two or three millimeter reduction in the amount of tibial bone loss in implantation of the artificial knee joint 10 according to this invention.

With particular reference to FIGS. 29-31, details of an alternative tibial component 140 and associated augment 170 are described. When a natural tibia T adjacent an artificial knee joint 10 has less than fully adequate bone volume directly adjacent the tibial component, it is desirable that at least a portion of the tibial component be augmented in thickness to make up for the absence of desirable bone volume. Often such tibial bone volume deficiency is limited to only a portion of the tibia T. With this invention, as shown in the embodiment of FIGS. 29-31, an augment 170 can be added to the alternative tibial component 140 on at least one half of the alternative tibial component 140 and a portion of the tibia T cut away to accommodate this augmented alternative tibial component 140.

In particular, the alternative tibial component 140 is similar to the tibial component 40 of the preferred embodiment, described above, except that the shaft 142 is depicted in this embodiment as tapering somewhat in diameter as it extends towards a tip, and is shown somewhat elongated. This shaft 142 variation is provided to illustrate the variety of different configurations for the shaft 140 that are within the scope of this invention. Similarly, the gussets 144 have a slightly different shape than that of the gussets 44 of the preferred embodiment described above. The alternative tibial component 140 includes a plate 150 similar in form and function to the plate 50 of the tibial component 40 described above.

Uniquely, the alternative tibial component 140 (FIGS. 29-31) includes threaded prongs 160 extending perpendicularly in a distal direction from the underside of the plate 150, and generally parallel with the shaft 142. These threaded prongs 160 have a pointed tip 162 and threads 164 on a cylindrical side thereof. When the alternative tibial component 140 is not required to be augmented with the augment 170, these threads 164 on the threaded prongs 160 can help assist bone in-growth and secure attachment of the tibia T to the alternative tibial component 140. If the alternative tibial component 140 requires augmentation, the augment 170 can be utilized on either side of the alternative tibial component 140, or two augments 170 can be provided, so that both sides of the alternative tibial component 140 are augmented in thickness.

The augment 170 preferably is a plate having a constant thickness between a substantially planar top surface 172 and a substantially planar bottom surface 174. A perimeter 176 extends between the top surface 172 and bottom surface 174. This perimeter 176 follows a contour of the underside of the plate 150. Because the plate 150 is bilaterally symmetrical, and because the top surface 172 and bottom surface 174 are both planar, and oriented parallel to each other, and the entire augment 170 is generally thin in form, it can be reversed to fit on either a left or right side of the alternative tibial component 140, merely be reversing the top surface 172 or the bottom surface 174.

The augment 170 includes slots 178 therein which can be aligned with the gussets 144 to help to stabilize the augment 170 and securely hold the augment 170 to the plate 150. Furthermore, the augment 170 preferably includes a pair of bores 175 aligning with two of the threaded prongs 160.

While the preferred embodiment shows two of these threaded prongs 160, it is conceivable that the augment 170 could be attached with only a single threaded prong 160 and the slots 178 and gussets 144 could coact together to prevent rotation of the augment 170 relative to the plate 150 about such a single prong 160.

The bores 175 preferably include steps 177 therein both at an upper and lower end of the bores 175. These steps 177 allow for recessing of nuts 188 as described in detail below.

The nuts 188 preferably have a generally cylindrical form with a threaded bore 182 on an interior portion thereof and with a face 186 on one end forming a flange 184 having a slightly greater diameter than other portions of the nut 180. This flange 184 has a diameter similar to that of the bores 175 at the step 177. Other portions of each nut 180 preferably have a diameter similar to that of the bores 175 spaced from the step 177. Each nut 180 can thus be recessed into the bore 175 with the flange 184 within the step 177 for complete recessing of the nuts 180.

A face 186 on each nut 180 preferably includes holes which can receive a torque applying tool so that the nuts 180 to be completely rotated into position. As an alternative to such holes, slits could be formed in the face 186, or other engagement structures could be provided on the face 186 to facilitate rotation of the nuts 180, even as they are being recessed into the bores 175 of the augment 170. Once one or more augments 170 are attached to the alternative tibial component 140, the augments 170 become part of the alternative tibial component 140 for implantation within the knee joint 10.

Referring to FIG. 31, a gap can be seen between the augment 170 and the plate 150 of the alternative tibial component 140. The plate 150 has a peripheral lip extending downwardly and against which the augment 170 comes into contact when the augment 170 is attached to the plate 150. Preferably, surfaces of the augment 170, including the surface 172 and the surface 174 include a peripheral rib extending perpendicularly from the surface 172 and the surface 174. These peripheral ribs extend perpendicularly from the surface and inboard of the perimeter 176 by a distance similar to a width of the peripheral lip on the plate 150, so that the peripheral rib is located inboard of the peripheral lip on the plate 150. This peripheral rib can thus help to keep the augment 170 precisely aligned where desired relative to the alternative tibial component 140. To further stabilize the augment 170, ribs having other patterns could also extend from the surfaces 172, 174 inboard of the peripheral rib to provide further contact between the augment 170 and the plate 150 and still maintain reversibility for the augment 170. One particular place for such ribs is surrounding the bores 175 to support the augment 170 at this attachment location.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A tibial component for an artificial knee joint, comprising in combination:
a shaft adapted to be located axially within a proximal end of a tibia;
a plate fixed to said shaft and oriented primarily within a plane substantially perpendicular to said shaft;
an insert adapted to be coupled to a proximal side of said plate opposite said shaft;
said insert adapted to support femoral loads thereon;
a dovetail rib extending up from said plate;
a dovetail recess in a distal surface of said insert, said dovetail recess sized to receive said dovetail rib therein;
wherein said insert includes a proximal surface having a pair of wells therein, each well adapted to receive a condylar structure therein;
wherein said wells each include a valley extending arcuately away from a low point within each said well, each of said valleys tapering upward away from a respective one of said low points of said wells with arcs each curving about a respective center point axis aligned with the low point of the other said well on said proximal surface of said insert, said valleys adapted to maintain alignment for passing of a condylar structure along one of said valleys while another condylar structure remains located within a low point of the other said well;
wherein said low point within each well defines a most distal portion of each well, with said proximal surface extending proximally in every direction away from each said well; and
wherein said valleys each exhibit a proximal slope away from said low point of each said well, as said valleys extend anteriorly from said low point of each said well.

2. The tibial component of claim 1 wherein said dovetail recess is open at a posterior end of said dovetail recess corresponding with a posterior end of the dovetail rib opposite an anterior end of the dovetail rib.

3. The jet component of claim 2 wherein said dovetail recess has an anterior end which stops short of an anterior side of said insert.

4. The tibial component of claim 3 wherein said dovetail rib has a length between an anterior end and a posterior end, said anterior end extending further proximally from said plate than said posterior end of said rib, such that a proximal height of said dovetail rib above proximal side of said plate tapers down from said anterior end of said rib to said posterior end of said rib.

5. The tibial component of claim 1 wherein said wells are symmetrical about a centerline between said wells, such that similar pivoting about each said condylar structure is accommodated; and
wherein said valleys taper proximally more gradually as said valleys extend in an anterior direction away from said low point than said valleys taper proximally as said valleys extend in a posterior direction, such that anterior rotation is accommodated more than posterior rotation.

6. The tibial component of claim 5 wherein said insert includes a distal surface opposite said proximal surface, said distal surface including lobes which extend distally from said distal surface, said lobes being semi-spherical in form, said lobes extending from said distal surface to an extent at least as great as a depth of said wells, with one of said lobes beneath each of said wells, such that material thickness of said insert is maintained without requiring the entire distal surface to extend distally as far as said lobes.

7. A tibial component for an artificial knee joint, comprising in combination:

a shaft adapted to be located axially within a proximal end of a tibia;
a plate coupled to said shaft and oriented primarily within a plane substantially perpendicular to said shaft;
an insert adapted to be coupled to a proximal side of said plate opposite said shaft;
said insert adapted to support femoral loads thereon;
a dovetail rib extending up from said plate;
a dovetail recess in a distal surface of said insert, said dovetail recess sized to receive said dovetail rib therein;
wherein said insert includes a proximal surface having a pair of wells therein, each well adapted to receive a condylar structure therein;
wherein said wells each include a valley extending arcuately away from a low point within each said well, each of said valleys tapering upward away from a respective one of said low points of said wells with arcs each curving about a respective center point axis aligned with the low point of the other said well on said proximal surface of said insert, said valleys adapted to maintain alignment for passing of a condylar structure along one of said valleys while another condylar structure remains located within a low point of the other said well;
wherein said low point within each well defines a most distal portion of each well, with said proximal surface extending proximally in every direction away from each said well; and
wherein said valleys each exhibit a proximal slope away from said low point of each said well, as said valleys extend anteriorly from said low point of each said well.

8. The tibial component of claim 7 wherein said dovetail recess is open at a posterior end of said dovetail recess corresponding with a posterior end of the dovetail rib opposite an anterior end of the dovetail rib.

9. The tibial component of claim 8 wherein said dovetail recess has an anterior end which stops short of an anterior side of said insert.

10. The tibial component of claim 9 wherein said dovetail rib has a length between an anterior end and a posterior end, said anterior end extending further proximally from said plate than said posterior end of said rib, such that a proximal height of said dovetail rib above proximal side of said plate tapers down from said anterior end of said rib to said posterior end of said rib.

11. The tibial component of claim 7 wherein said wells are symmetrical about a centerline between said wells, such that similar pivoting about each said condylar structure is accommodated; and
wherein said valleys taper proximally more gradually as said valleys extend in an anterior direction away from said low point that said valleys taper proximally as said valleys extend in a posterior direction, such than anterior rotation is accommodated more than posterior rotation.

12. The tibial component of claim 11 wherein said insert includes a distal surface opposite said proximal surface, said distal surface including lobes which extend distally from said distal surface, said lobes being substantially semi-spherical in form, said lobes extending from said distal surface to an extent at least as great as a depth of said wells, with one of said lobes beneath each of said wells, such that material thickness of said insert is maintained without requiring the entire distal surface to extend distally as far as said lobes.

13. A tibial component for an artificial knee joint, comprising in combination:
a shaft adapted to be located axially within a proximal end of a tibia;
a plate fixed to said shaft and oriented primarily within a plane substantially perpendicular to said shaft;
an insert adapted to be coupled to a proximal side of said plate opposite said shaft;
said insert adapted to support femoral loads thereon;
a dovetail rib extending up from said plate, said dovetail rib having a length between an anterior end and a posterior end, said anterior end extending further proximally from said plate than said posterior end of said rib, such that a proximal height of said dovetail rib above proximal side of said plate tapers down from said anterior end of said rib to said posterior end of said rib;
a dovetail recess in a distal surface of said insert, said dovetail recess sized to receive said dovetail rib therein;
wherein said proximal side of said plate includes depressions therein, one on either side of said dovetail rib, and said insert includes a distal surface having lobes thereon, said lobes sized to fit within said depressions in said plate;
wherein said insert includes a proximal surface having a pair of symmetrical wells therein, each well adapted to receive a condylar structure therein
wherein said wells each include a valley extending arcuately away from a low point within each said well, each of said valleys tapering upward away from a respective one of said low points of said wells with arcs each curving about a respective center point axis aligned with the low point of the other said well on said proximal surface of said insert, said valleys adapted to maintain alignment for passing of a condylar structure along one of said valleys while another condylar structure remains located within a low point of the other said well;
wherein said low point within each well defines a most distal portion of each well, with said proximal surface extending proximally in every direction away from each said well; and
wherein said valleys each exhibit a proximal slope away from said low point of each said well, as said valleys extend anteriorly from said low point of each said well.

14. The tibial component of claim 13 wherein said dovetail rib includes two opposing substantially parallel side walls extending proximally from said plate and forming a lower portion of said dovetail rib adjacent said proximal surface of said plate.

15. The tibial component of claim 14 wherein said dovetail rib includes beveled walls on opposite sides of said dovetail rib above said side walls and extending up to a top wall of said dovetail rib, said beveled walls having a constant distance between said top wall and portions of said beveled walls adjacent said side walls, this constant distance maintained from said anterior end to said posterior end and said side wall tapering from a greater height up from said plate at said anterior end to a lesser height up from said plate at said posterior end.

16. The tibial component of claim 15 wherein said dovetail rib merges into a posterior wall extending laterally generally perpendicular to said dovetail rib, said insert adapted to abut said posterior wall when said dovetail recess of said insert has been fully slid onto said dovetail rib of said plate.

17. The tibial component of claim 16 wherein an anterior clip extends up from said proximal surface of said plate at a location spaced from said anterior end of said dovetail rib, said anterior clip having a tooth, said insert including a recess therein adapted to receive said anterior clip therein when said insert has been fully located upon said plate with said dovetail rib within said dovetail recess.

18. The tibial component of claim 13 wherein an anterior clip extends up from said proximal surface of said plate at a location spaced from said anterior end of said dovetail rib, said anterior clip having a tooth, said insert including a recess therein adapted to receive said anterior clip therein when said insert has been fully located upon said plate with said dovetail rib within said dovetail recess.

\* \* \* \* \*